US012156944B2

(12) United States Patent
Aleksiev et al.

(10) Patent No.: US 12,156,944 B2
(45) Date of Patent: Dec. 3, 2024

(54) ORAL PHARMACEUTICAL COMPOSITION WITH A PLANT ALKALOID FOR TREATMENT OF DEPENDENCIES

(71) Applicant: SOPHARMA AD, Sofia (BG)

(72) Inventors: Angel Aleksiev Aleksiev, Sofia (BG); Veselin Evgeniev Daskalov, Sofia (BG)

(73) Assignee: SOPHARMA AD

(*) Notice: Subject to any disclaimer, the term of this patent is extended or adjusted under 35 U.S.C. 154(b) by 0 days.

(21) Appl. No.: 17/328,911

(22) Filed: May 24, 2021

(65) Prior Publication Data

US 2021/0275460 A1   Sep. 9, 2021

Related U.S. Application Data

(63) Continuation of application No. PCT/BG2019/000027, filed on Nov. 28, 2019.

(30) Foreign Application Priority Data

Apr. 12, 2019 (BG) ........................................ 112910

(51) Int. Cl.

| A61K 9/48 | (2006.01) |
|---|---|
| A61K 9/20 | (2006.01) |
| A61K 31/14 | (2006.01) |
| A61K 31/405 | (2006.01) |
| A61K 31/439 | (2006.01) |
| A61K 31/444 | (2006.01) |
| A61K 31/445 | (2006.01) |
| A61K 31/55 | (2006.01) |

(52) U.S. Cl.
CPC .......... *A61K 9/2054* (2013.01); *A61K 9/2009* (2013.01); *A61K 9/485* (2013.01); *A61K 9/4866* (2013.01); *A61K 31/14* (2013.01); *A61K 31/405* (2013.01); *A61K 31/439* (2013.01); *A61K 31/444* (2013.01); *A61K 31/445* (2013.01); *A61K 31/55* (2013.01)

(58) Field of Classification Search
None
See application file for complete search history.

(56) References Cited

U.S. PATENT DOCUMENTS

| 5,414,005 | A | 5/1995 | Schneider et al. | |
|---|---|---|---|---|
| 6,534,527 | B2 | 3/2003 | Wolfson et al. | |
| 7,094,787 | B2 | 8/2006 | Okubo et al. | |
| 9,387,172 | B2 * | 7/2016 | Wahl | A61P 25/34 |
| 2005/0123502 | A1 * | 6/2005 | Chan | A61K 31/785 |
| | | | | 514/343 |
| 2008/0103111 | A1 | 5/2008 | Bieley | |
| 2008/0145422 | A1 | 6/2008 | Zhou et al. | |
| 2010/0021570 | A1 * | 1/2010 | Bieley | A61K 31/198 |
| | | | | 424/729 |
| 2011/0098265 | A1 * | 4/2011 | Bull | A61K 31/4748 |
| | | | | 514/188 |
| 2016/0340334 | A1 * | 11/2016 | Knight | A61K 31/475 |
| 2019/0175610 | A1 * | 6/2019 | Clouatre | A61K 31/55 |

FOREIGN PATENT DOCUMENTS

| BG | 65536 | B1 * | 11/2008 | ............ A61P 25/00 |
|---|---|---|---|---|
| CN | 101342173 | | 1/2009 | |
| CN | 107744508 | | 3/2018 | |
| EP | 0449247 | | 10/1991 | |
| EP | 1586320 | | 10/2005 | |
| EP | 2957280 | | 12/2015 | |
| EP | 2957280 | A1 * | 12/2015 | ........... A61K 31/198 |
| RU | 2125883 | | 2/1999 | |
| RU | 2134585 | | 8/1999 | |
| RU | 2157704 | | 10/2000 | |
| RU | 2571720 | | 12/2015 | |
| RU | 2593362 | | 8/2016 | |

(Continued)

OTHER PUBLICATIONS

International Search Report and Written Opinion mailed Mar. 26, 2020 for PCT/BG2019/000027.
Closs et al., "Effect of Magnesium Stearate on a Pharmaceutical Blend Using Thermal Effusivity," Materials Science (2004).
Jacob et al., "Factors Affecting the Dissolution Rate of Medicaments from Tablets II," Journal of Pharmaceutical Sciences, 57(5):802-805 (May 1968).
Mattsson, Sofia, "Pharmaceutical binders and their function in directly compressed tablets: Mechanistic studies on the effect of dry binders on mechanical strength, pore structure and disintegration of tablets," (2000).
Uzunović et al., "Effect of magnesium stearate concentration on dissolution properties of ranitidine hydrochloride coated tablets," Bosn J Basic Med Sci., 7(3):279-83 (Aug. 2007).

*Primary Examiner* — Susan T Tran
(74) *Attorney, Agent, or Firm* — Perkins Coie LLP

(57) ABSTRACT

This invention is related to an oral pharmaceutical composition that contains a cholinergic agent, a natural plant alkaloid in particular, selected from the group of lobeline, anabasine, cytisine, galantamine or their acceptable salts, in the form of tablets and capsules. The excipients of the developed oral composition include cellulose powder, calcium sulphate, silica colloidal and magnesium stearate, the total content of cellulose powder and calcium sulphate dihydrate being from 64.5 to 97.5% of the mass of the dosage form and at least 90% of the alkaloid particles being ≤100 µm. The oral composition contains also at least one biologically active amino acid selected from: L-carnitine, tryptophan or a combination of them.
The oral composition according to this invention achieves uniform distribution of the active substance in the composition, as well as stability of the composition due to the included excipients selected so as to react to a minimum with the alkaloid to form the qualitative and quantitative related substances admissible for the pharmaceutical composition.
The composition according to this invention is applicable in the treatment of dependency and addiction to nicotine, tobacco products and alcohol.

3 Claims, No Drawings

(56) References Cited

FOREIGN PATENT DOCUMENTS

| RU | 2593585 | 8/2016 | |
|---|---|---|---|
| WO | WO 1994/016708 | 8/1994 | |
| WO | WO 2000/038686 | 7/2000 | |
| WO | WO 2007/146115 | 12/2007 | |
| WO | WO 2010/070091 | 6/2010 | |
| WO | WO 2011/064797 | 6/2011 | |
| WO | WO-2011064797 A2 * | 6/2011 | ........... A61K 9/2018 |
| WO | WO 2013/109961 | 7/2013 | |
| WO | WO 2014/076680 | 5/2014 | |
| WO | WO 2016/018178 | 2/2016 | |

* cited by examiner

ORAL PHARMACEUTICAL COMPOSITION WITH A PLANT ALKALOID FOR TREATMENT OF DEPENDENCIES

CROSS REFERENCE TO RELATED APPLICATIONS

This application is a continuation of International Application No. PCT/BG2019/000027 filed on Nov. 28, 2019, which claims priority to Bulgaria Application No. 112910 filed on Apr. 12, 2019, the entireties of each of which are incorporated herein by reference.

TECHNICAL FIELD

This invention is related to an oral pharmaceutical composition that contains a cholinergic agent, a natural plant alkaloid in particular, selected from the group of cytisine, galantamine, lobeline, anabasine or their acceptable salts, which is used in the treatment of dependency and addiction to nicotine, tobacco products and alcohol.

BACKGROUND

Alcohol and nicotine like all drugs possess the potential to form and maintain dependency. By their direct effect on the cells, including nerve cells and their transmission systems (the so-called neurotransmitters—acetylcholine, dopamine, serotonin), due to the systemic intake of the relevant substance, a condition occurs called "dependence syndrome"— physical and mental. The central and peripheral nervous systems (CNS and PNS) belong to those organ systems where alcohol and nicotine influence various and intensive effect resulting in complex symptoms that lead to a significant decrease of working capacity and/or social activity of the patient. Physical dependence on substances is due to their participation in the biochemical body processes, and the psychological one is based on the fact that cigarette smoking and alcohol at small doses tone up, and improve the mood by activation of brain structures, the so-called "reward pathways" (stimulation of neurons of these structures). Both components of addiction are interrelated, but mental dependence remains dominating and lasts longer.

A controlled pharmaceutical form of WO2000/038686 is known that contains the alkaloid of galantamine hydrobromide in a quantity of 5 to 40 mg and a water-soluble polymer in 1:1 proportion, intended for use in addiction to substances, as well as in nicotine cessation and withdrawal.

WO9416708 is known transdermal, oral and parenteral use of galantamine or its salts in a quantity of 0.1 to 50% by weight, In particular 2-15% by weight, for treatment of nicotine dependence.

From the EP0449247 is known the use of galantamine or its salts for manufacture of a medication that contains 5-20% preferably of the mass of the contents for treatment of alcoholism.

There are also known products based on plant extracts, homeopathic agents, based on essential oils and complexes (in the form of chewing gum patch, cigarette, tablets, candies, etc.)—"Korida" (RU 2134585), "Koldunok" (RU 2125883), "Antinikotin" (RU 2157704). Devices based on vitamins and amino-acids are also used (U.S. Pat. No. 7,094,787, US 2008103111).

There is also a popular alternative of traditional cigarettes in the form of nicotine-replacing cytisine-containing liquid products for electronic cigarettes (RU 2593362) or intranasal spraying (RU 2593585).

Anti-nicotine devices based on nicotine and alkaloids with nicotine-like effect are widely known, i.e., "Tabex," "Lobesil," "Gamibazin," Nicorette, Nikotinell, etc. They are available various forms—tablets, chewing gum, cigarette, transdermal systems, etc.

It is known also a medicinal product against smoking in the form of film-tablets (EP 1 586 320 B1), each tablet containing 1.5 mg of cytisine and excipients: microcrystalline cellulose, lactose, talc, magnesium stearate and film-coating, used in nicotine dependence.

From the RU 2572720 is known a complex antinicotinic device that contains an alkaloid with nicotine-like effect selected from: nicotine hydrochloride in a quantity of 1-1.5 mg per dose, lobeline 1-1.5 mg, anabasine hydrochloride 1-2 mg and cytisine 0.5-1 mg, as well as theanine and tryptophan, in the form of tablets (for chewing or for sucking), chewing gums and chewing candies. The described tablet contains the excipients mannitol, microcrystalline cellulose, povidone, methyl cellulose, magnesium stearate, flavour, aspartame, the active substance being added to the tablet mass during the stage of granulation.

This composition of the tablet mass difficulty provides the required uniformity of the alkaloid content, as well as the masking of the bitter taste of the tablet during sucking, and also the uniformity and dissolution of the alkaloid in the mouth and hides the risk of overdose.

The specific problem appeared with the solid forms is the segregation of the participating substances, which later results in differences in the distribution of the substances in the composition of the solid form. Segregation is even more unacceptable when a cholinergic agent is used, i.e., an alkaloid, as an active substance. In such cases, when the active substance is an alkaloid, its concentration is lower because at higher doses it is toxic; the proper and uniform distribution of active substance particles in the composition, the so-called uniformity of active substance content, is important together with ensuring the required level of dissolution of the alkaloid from the dosage form, and its disintegration, which is an important prerequisite for ensuring good or improved bioavailability.

SUMMARY

According to the present invention an oral composition is obtained that contains a cholinergic agent, a natural plant alkaloid in particular, selected from the group of: lobeline, anabasine, cytisine, galantamine or their acceptable salts in a quantity of mg per dose, i.e.: cytisine from 1.5 to 3.0; galantamine from 5 to 20; lobeline from 1.5 to 2.0; anabasine from 1.5 to 3.0 or their acceptable salts, and excipients that include: cellulose powder, calcium sulphate, silica colloidal and magnesium stearate, the total content of cellulose powder and calcium sulphate being from 64.5 to 97.5% of the mass of the dosage form and at least 90% of the alkaloid particles being ≤100 μm.

The excipients of the oral composition of this invention are in a quantity of mass percentage as follows: cellulose powder from 5.0 to 92.5%, calcium sulphate dihydrate from 5.0 to 92.5%, silica colloidal anhydrous from 0.5 to 3.0% and magnesium stearate in a quantity from 0.5 to 3.0%.

Another variation of this invention additionally contains at least one biologically active amino acid selected from: L-carnitine, tryptophan or a combination of them in quantities in mg: for L-carnitine of 0.2-0.4 and tryptophan from 5 to 55.

The natural amino acid—carnitine and its esters (selected from L-carnitine hydrochloride, carnitine tartrate, L-carnitine base, acetyl-L-carnitine), enhances fat metabolism, especially in treatment of nicotine dependence in individuals having a capacity to weight gain by protecting them from the fast increasement of body weight, since smoking cessation results in delay of metabolism.

Tryptophan includes 1-tryptophan, 5-hydroxytryptophan and other biologically active forms and derivatives of the substance. Preferably tryptophan should be in a quantity from 20 to 40 mg.

The oral composition according to this invention can be used in a solid dosage form intended for oral administration in the form of tablets and capsules.

The compounds of the alkaloids can be used in the form of salts (for example, as a chloride, sulphate, tartrate, fumarate, citrate, maleate, lactate, hydrobromide or aspartate).

The oral composition according to this invention achieves uniform distribution of the active substance in the composition—the tests of uncoated tablets and capsules have not established any deviations in the alkaloid content out of ±5.0% of the average alkaloid content. The achieved stability of the composition is due to the included new excipients—calcium sulphate and cellulose powder, as well as to the appropriate selection of all excipients and their quantities. The included excipients have been selected in this way to react to a minimum with the alkaloid and to form the qualitative and quantitative related substances admissible for the pharmaceutical composition. The created oral composition (tablets, capsules) has a level of alkaloid dissolution not less than 75% after 45 minutes and good disintegration (Tables 1-5). The composition permits also a high level of active substance dissolution, as well as maintenance of low levels of the single impurity of the alkaloid during storage.

The finished tablets/capsules comply with present-day pharmacopoeial requirements. Elimination of two excipients—MCC and lactose results also in an economic effect—lowering of production costs.

Carnitine added in the oral composition according to the invention increases product efficacy by protecting the patient from fast increase of its body weight. Acetyl-L-carnitine in particular is a precursor of acetylcholine with neuroprotective and antioxidant properties; it successfully improves the mood in adults and presents a positive effect in suppression of depressive conditions.

The added biologically active amino acid Tryptophan enhances also product efficacy by supporting and correcting mental disturbances during the abstinence syndrome and decreases the risk of side effects in abstinence, uplifts the mood, the sense of happiness, decreases the sense of anxiety and fear as well as the craving for nicotine and alcohol.

The natural plant alkaloids used are in an efficient form and quantity so as to demonstrate or manifest their potential.

The uniform distribution of the alkaloid provides its relatively constant concentration in patient's body at a level sufficient to activate the acetylcholine (nicotine) receptors responsible for the therapeutic effect as well as assure sufficient activity of the alkaloid (agonist) responsible for activation of relevant neurons that induce the secretion of suitable neurotransmitters.

The ensured therapeutic effect of the oral composition according to the invention is expressed in the treatment of dependency and addiction to nicotine, tobacco products and alcohol.

EXAMPLES

The oral composition is illustrated but not limited to the following examples where the quantities of the substances per dose are presented in mg:

Examples 1-9

| composition | 1 | 2 | 3 | 4 | 5 | 6 | 7 | 8 | 9 |
|---|---|---|---|---|---|---|---|---|---|
| Cytisine | 1.5 | 1.5 | 1.5 | 1.5 | 1.5 | 1.5 | 1.5 | 1.5 | 1.5 |
| Galantamine HBr | — | — | — | — | — | — | — | — | — |
| Anabasine HCl | — | — | — | — | — | — | — | — | — |
| Lobeline HCl | — | — | — | — | — | — | — | — | — |
| L- carnitine | — | — | — | — | 0.3 | — | 0.2 | — | — |
| Tryptophan | — | — | — | — | — | 25.0 | 30,0 | — | — |
| Cellulose powder | 5.0 | 5.0 | 5.0 | 5.0 | 92.2 | 59.8 | 60.0 | 84.5 | 61.5 |
| Calcium sulphate dihydrate | 92.5 | 90.0 | 90.0 | 87.5 | 5.0 | 5.0 | 5.0 | 8.0 | 35.0 |
| Magnesium stearate | 0.5 | 0.5 | 3.0 | 3.0 | 0.5 | 0.5 | 3.0 | 3.0 | 1.0 |
| Silica colloidal anhydrous | 0.5 | 3.0 | 0.5 | 3.0 | 0.5 | 3.0 | 0.5 | 3.0 | 1.0 |
| Total weight | 100.0 | 100.0 | 100.0 | 100.0 | 100.0 | 100.0 | 100.0 | 100.0 | 100.0 |
| Film-coating | 2.0 | 3.0 | — | 4.0 | 5.0 | — | 2.0 | — | 3.0 |

Examples 10-18

| composition | 10 | 11 | 12 | 13 | 14 | 15 | 16 | 17 | 18 |
|---|---|---|---|---|---|---|---|---|---|
| Cytisine | 3.0 | 3.0 | 3.0 | 3.0 | 3.0 | 3.0 | 3.0 | 3.0 | 3.0 |
| Galantamine HBr | — | — | — | — | — | — | — | — | — |
| Anabasine HCl | — | — | — | — | — | — | — | — | — |
| Lobeline HCl | — | — | — | — | — | — | — | — | — |
| L- carnitine | — | — | — | — | — | 0.3 | 0.2 | — | — |
| Tryptophan | — | — | — | — | — | — | 10 | — | — |
| Cellulose powder | 5.0 | 5.0 | 5.0 | 5.0 | 91.0 | 88.2 | 78.3 | 175.0 | 10.0 |
| Calcium sulphate dihydrate | 91.0 | 88.5 | 88.5 | 86.0 | 5.0 | 5.0 | 5.0 | 10.0 | 180.0 |
| Magnesium stearate | 0.5 | 0.5 | 3.0 | 3.0 | 0.5 | 0.5 | 3.0 | 6.0 | 1.0 |
| Silica colloidal anhydrous | 0.5 | 3.0 | 0.5 | 3.0 | 0.5 | 3.0 | 0.5 | 6.0 | 6.0 |

-continued

| composition | 10 | 11 | 12 | 13 | 14 | 15 | 16 | 17 | 18 |
|---|---|---|---|---|---|---|---|---|---|
| Total weight | 100.0 | 100.0 | 100.0 | 100.0 | 100.0 | 100.0 | 100.0 | 200.0 | 200.0 |
| Film-coating | — | 3.0 | 4.0 | — | 5.0 | 2.0 | — | 4.0 | — |

Examples 19-27

| composition | 19 | 20 | 21 | 22 | 23 | 24 | 25 | 26 | 27 |
|---|---|---|---|---|---|---|---|---|---|
| Cytisine | — | — | — | — | — | — | — | — | — |
| Galantamine HBr | 5.0 | 5.0 | 5.0 | 5.0 | 5.0 | 5.0 | 5.0 | 5.0 | 5.0 |
| Anabasine HCl | — | — | — | — | — | — | — | — | — |
| Lobeline HCl | — | — | — | — | — | — | — | — | — |
| L-carnitine | — | — | — | — | 0.3 | 0.2 | — | — | — |
| Tryptophan | — | — | — | — | — | 10.0 | — | — | — |
| Cellulose powder | 5.0 | 5.0 | 5.0 | 5.0 | 88.7 | 76.3 | 86.5 | 84.0 | 47.0 |
| Calcium sulphate dihydrate | 89.0 | 86.5 | 86.5 | 84.0 | 5.0 | 5.0 | 5.0 | 5.0 | 45.0 |
| Magnesium stearate | 0.5 | 0.5 | 3.0 | 3.0 | 0.5 | 0.5 | 3.0 | 3.0 | 1.5 |
| Silica colloidal anhydrous | 0.5 | 3.0 | 0.5 | 3.0 | 0.5 | 3.0 | 0.5 | 3.0 | 1.5 |
| Total weight | 100.0 | 100.0 | 100.0 | 100.0 | 100.0 | 100.0 | 100.0 | 100.0 | 100.0 |
| Film-coating | — | 3.0 | 4.0 | — | 5.0 | 2.0 | — | 4.0 | — |

Examples 27-36

| composition | 28 | 29 | 30 | 31 | 32 | 33 | 34 | 35 | 36 |
|---|---|---|---|---|---|---|---|---|---|
| Cytisine | — | — | — | — | — | — | — | — | — |
| Galantamine HBr | 10.0 | 10.0 | 10.0 | 10.0 | 10.0 | 10.0 | 10.0 | 10.0 | 20.0 |
| Anabasine HCl | — | — | — | — | — | — | — | — | — |
| Lobeline HCl | — | — | — | — | — | — | — | — | — |
| L-carnitine | — | — | — | — | 0.3 | 0.2 | — | — | — |
| Tryptophan | — | — | — | — | — | 5.0 | — | — | — |
| Cellulose powder | 5.0 | 5.0 | 5.0 | 5.0 | 83.7 | 76.3 | 81.5 | 79.0 | 22.0 |
| Calcium sulphate dihydrate | 84.0 | 81.5 | 81.5 | 79.0 | 5.0 | 5.0 | 5.0 | 5.0 | 55.0 |
| Magnesium stearate | 0.5 | 0.5 | 3.0 | 3.0 | 0.5 | 0.5 | 3.0 | 3.0 | 1.5 |
| Silica colloidal anhydrous | 0.5 | 3.0 | 0.5 | 3.0 | 0.5 | 3.0 | 0.5 | 3.0 | 1.5 |
| Total weight | 100.0 | 100.0 | 100.0 | 100.0 | 100.0 | 100.0 | 100.0 | 100.0 | 100.0 |
| Film-coating | 2.0 | 3.0 | — | 4.0 | 5.0 | — | 2.0 | — | 3.0 |

Examples 37-45

| composition | 37 | 38 | 39 | 40 | 41 | 42 | 43 | 44 | 45 |
|---|---|---|---|---|---|---|---|---|---|
| Cytisine | — | — | — | — | — | — | — | — | — |
| Galantamine HBr | 20.0 | 20.0 | 20.0 | 20.0 | 20.0 | 20.0 | 20.0 | 20.0 | 20.0 |
| Anabasine HCl | — | — | — | — | — | — | — | — | — |
| Lobeline HCl | — | — | — | — | — | — | — | — | — |
| L-carnitine | — | — | — | — | 0.3 | 0.2 | — | — | — |
| Tryptophan | — | — | — | — | — | 30.0 | — | — | — |
| Cellulose powder | 10.0 | 10.0 | 10.0 | 10.0 | 167.7 | 132.8 | 163.0 | 158.0 | 10.0 |
| Calcium sulphate dihydrate | 168.0 | 163.0 | 163.0 | 158.0 | 10.0 | 10.0 | 10.0 | 10.0 | 168.0 |
| Magnesium stearate | 1.0 | 1.0 | 6.0 | 6.0 | 1.0 | 1.0 | 6.0 | 6.0 | 1.0 |
| Silica colloidal anhydrous | 1.0 | 6.0 | 1.0 | 6.0 | 1.0 | 6.0 | 1.0 | 6.0 | 1.0 |
| Total weight | 200.0 | 200.0 | 200.0 | 200.0 | 200.0 | 200.0 | 200.0 | 200.0 | 200.0 |
| Film-coating | — | 3.0 | 4.0 | — | 5.0 | 2.0 | — | 4.0 | — |

Examples 46-54

|  | Examples No | | | | | | | | |
|---|---|---|---|---|---|---|---|---|---|
| composition | 46 | 47 | 48 | 49 | 50 | 51 | 52 | 53 | 54 |
| Cytisine | — | — | — | — | — | — | — | — | — |
| Galantamine HBr | — | — | — | — | — | — | — | — | — |
| Anabasine HCl | 2.0 | 2.0 | 2.0 | 2.0 | 2.0 | 2.0 | 2.0 | 2.0 | 2.0 |
| Lobeline HCl | — | — | — | — | — | — | — | — | — |
| L-carnitine | — | — | — | — | — | 0.3 | 0.2 | — | — |
| Tryptophan | — | — | — | — | — | — | — | 30 | 30.0 |
| Cellulose powder | 5.0 | 5.0 | 5.0 | 5.0 | 92.0 | 89.2 | 59.3 | 146.0 | 10.0 |
| Calcium sulphate dihydrate | 92.0 | 89.5 | 89.5 | 87.0 | 5.0 | 5.0 | 5.0 | 10.0 | 181.0 |
| Magnesium stearate | 0.5 | 0.5 | 3.0 | 3.0 | 0.5 | 0.5 | 3.0 | 6.0 | 1.0 |
| Silica colloidal | 0.5 | 3.0 | 0.5 | 3.0 | 0.5 | 3.0 | 0.5 | 6.0 | 6.0 |
| Total weight | 100.0 | 100.0 | 100.0 | 100.0 | 100.0 | 100.0 | 100.0 | 200.0 | 200.0 |
| Film-coating | — | 3.0 | 4.0 | — | 5.0 | 2.0 | — | 4.0 | — |

Examples 54-63

|  | Examples No | | | | | | | | |
|---|---|---|---|---|---|---|---|---|---|
| composition | 55 | 56 | 57 | 58 | 59 | 60 | 61 | 62 | 63 |
| Cytisine | — | — | — | — | — | — | — | — | — |
| Galantamine HBr | — | — | — | — | — | — | — | — | — |
| Anabasine HCl | — | — | — | — | — | — | — | — | — |
| Lobeline HCl | 3.0 | 3.0 | 3.0 | 3.0 | 3.0 | 3.0 | 3.0 | 3.0 | 3.0 |
| L-carnitine | — | — | — | — | — | 0.3 | 0.2 | — | — |
| Tryptophan | — | — | — | — | — | — | — | 30 | — |
| Cellulose powder | 5.0 | 5.0 | 5.0 | 5.0 | 91.0 | 88.5 | 84.5 | 175.0 | 10.0 |
| Calcium sulphate dihydrate | 91.0 | 88.5 | 88.5 | 86.0 | 5.0 | 5.0 | 9.0 | 10.0 | 180.0 |
| Magnesium stearate | 0.5 | 0.5 | 3.0 | 3.0 | 0.5 | 0.5 | 3.0 | 6.0 | 1.0 |
| Silica colloidal anhydrous | 0.5 | 3.0 | 0.5 | 3.0 | 0.5 | 3.0 | 0.5 | 6.0 | 6.0 |
| Total weight | 100.0 | 100.0 | 100.0 | 100.0 | 100.0 | 100.0 | 100.0 | 200.0 | 200.0 |
| Film-coating | — | 3.0 | 4.0 | — | 5.0 | 2.0 | — | 4.0 | — |

The natural alkaloids used in the examples above are isolated from the relevant plant species, i.e., anabasine—isolated from *Anabasis aphylla* L., lobeline—from *Lobelia inflata*, cytisine—from the seeds of *Cytisus laburnum* L., Golden chain or *Thermopsis lanceolata* R. Br, and galantamine—isolated from *Leucojum aestivum* L or *Narcissus* Carlon cv.

According to the examples, the pharmaceutical mixture for the oral pharmaceutical composition, is obtained by a classical method, the described alkaloid quantity being mixed with the required quantity of cellulose powder, then added to the mixer and the relevant quantity of calcium sulphate dihydrate, silica colloidal and magnesium stearate and homogenized. In some cases, the required quantity of L-carnitine and/or tryptophan is added. The obtained mixture is suitable for dosing in hard capsules using capsule automat or tableted in a tablet press, the obtained tablet cores being subject to film coating.

TABLE NO 1

Product: 1.5 mg film-coated tablets of cytisine obtained according to Example 3
Batch No E14P5S 10713
Storage conditions: Temperature: (25 ± 2)° C.; Relative humidity: (60 ± 5)%

| No | Test items | Specification and standards | 0 months | 3 months | 6 months | 9 months | 12 months | 18 months | 24 months |
|---|---|---|---|---|---|---|---|---|---|
| 1. | Appearance | Round, biconvex film-coated tablets, diameter 6 mm | Complies | Complies | Complies | Complies | Complies | Complies | Complies |
| 2. | Colour | Beige | Complies | Complies | Complies | Complies | Complies | Complies | Complies |
| 3. | Disintegration, min, not more than | 30 | 2 | 2 | 2 | 2 | 2 | 2 | 2 |
| 4. | Dissolution of cytisine, per cent of the stated content after 45 min, not less than | Q = 75.0 | 95.4 | 92.5 | 96.5 | 95.8 | 93.1 | 94.6 | 90.8 |

TABLE NO 1-continued

Product: 1.5 mg film-coated tablets of cytisine obtained according to Example 3
Batch No E14P5S 10713
Storage conditions: Temperature: (25 ± 2)° C.; Relative humidity: (60 ± 5)%

| No | Test items | Specification and standards | 0 months | 3 months | 6 months | 9 months | 12 months | 18 months | 24 months |
|---|---|---|---|---|---|---|---|---|---|
| 5. | Related substances, per cent, not more than: | | | | | | | | |
|  | N-formylcytisine | 0.5 | BDL | 0.06 | 0.06 | 0.08 | 0.11 | 0.15 | 0.16 |
|  | any impurity | 0.2 | 0.08 | 0.08 | 0.08 | 0.08 | 0.08 | 0.10 | 0.08 |
|  | total impurities | 1.5 | 0.08 | 0.14 | 0.14 | 0.16 | 0.19 | 0.28 | 0.26 |
| 6. | Assay of cytisine in one film-coated tablet, mg | From 1.425 to 1.575 | 1.470 | 1.448 | 1.456 | 1.445 | 1.440 | 1.410 | 1.417 |
| 7. | Microbiological quality | To comply with the test | Complies | Complies | Complies | Complies | Complies | Complies | Complies |

BDL—below detectable level;

TABLE NO 2

Product: 3.0 mg film-coated tablets of cytisine obtained according to Example 14
Batch No E14P5S 20713
Storage conditions: Temperature: (25 ± 2)° C.; Relative humidity: (60 ± 5)%

| No | Test items | Specification and standards | 0 months | 3 months | 6 months | 9 months | 12 months | 18 months | 24 months |
|---|---|---|---|---|---|---|---|---|---|
| 1. | Appearance | Round, biconvex film-coated tablets, diameter 6 mm | Complies | Complies | Complies | Complies | Complies | Complies | Complies |
| 2. | Colour | Beige | Complies | Complies | Complies | Complies | Complies | Complies | Complies |
| 3. | Disintegration, min, not more than | 30 | 2 | 2 | 2 | 2 | 3 | 3 | 2 |
| 4. | Dissolution of cytisine, per cent of the stated content after 45 min, not less than | Q = 75.0 | 94.4 | 98.9 | 94.8 | 93.6 | 92.9 | 95.8 | 94.5 |
| 5. | Related substances, per cent, not more than: | | | | | | | | |
|  | N-formylcytisine | 0.5 | BDL | 0.05 | 0.07 | 0.09 | 0.11 | 0.16 | 0.16 |
|  | any impurity | 0.2 | BDL | BDL | BDL | 0.07 | 0.06 | 0.09 | 0.08 |
|  | total impurities | 1.5 | 0 | 0.05 | 0.07 | 0.16 | 0.17 | 0.26 | 0.25 |
| 6. | Assay of cytisine in one film-coated tablet, mg | From 2.850 to 3.150 | 2.969 | 2.972 | 2.940 | 2.950 | 2.950 | 2.912 | 2.936 |
| 7. | Microbiological quality | To comply with the test | Complies | Complies | Complies | Complies | Complies | Complies | Complies |

BDL—below detectable level;

TABLE NO 3

Composition with galantamine hydrobromide 10 mg tablets, obtained according to Example 34
Monitored batch: 10312
Storage conditions: (25 ± 2)° C./(60 ± 5)% RH
Package: Blister - green, semi-transparent PVC and aluminium film

| Test items | Standard | 0 months | 3 months | 6 months | 9 months | 12 months | 18 months | 24 months | 36 months | 48 months | 60 months |
|---|---|---|---|---|---|---|---|---|---|---|---|
| 1. Disintegration, min, not more than | 15 | 1 | 1 | 1 | 1 | 1 | 1 | 1 | 1 | 1 | 1 |
| 2. Dissolution of galantamine hydrobromide, %, of the stated content in 30 min, not less than | 75 (Q) | 98.8 | 102.1 | 98.0 | 102.1 | 96.8 | 106.0 | 103.4 | 97.1 | 103.6 | 95.8 |
| 3. Related substances, %, not more than: | | | | | | | | | | | |
| impurity E (N-desmethylgalantamine) | 0.6 | 0.22 | 0.20 | 0.23 | 0.25 | 0.23 | 0.22 | 0.23 | 0.20 | 0.24 | 0.24 |

TABLE NO 3-continued

Composition with galantamine hydrobromide 10 mg tablets, obtained according to Example 34
Monitored batch: 10312
Storage conditions: (25 ± 2)° C./(60 ± 5)% RH
Package: Blister - green, semi-transparent PVC and aluminium film

| Test items | Standard | 0 months | 3 months | 6 months | 9 months | 12 months | 18 months | 24 months | 36 months | 48 months | 60 months |
|---|---|---|---|---|---|---|---|---|---|---|---|
| unspecified impurity | 0.2 | 0.05 | 0.05 | 0.07; 0.05 | 0.07; 0.05 | 0.05 | 0.06 | 0.07; 0.05 | 0.05 | 0.06; 0.07 | 0.06; 0.07 |
| total impurities | 1.5 | 0.27 | 0.25 | 0.35 | 0.37 | 0.28 | 0.28 | 0.35 | 0.25 | 0.37 | 0.37 |
| Assay of galantamine in one film-coated tablet, mg | from 9.5 to 10.5 | 9.962 | 9.972 | 9.975 | 9.850 | 9.750 | 9.880 | 9.798 | 9.890 | 9.880 | 9.820 |

TABLE 4

Composition with galantamine hydrobromide 10 mg capsules, according to Example 31

| Monitor batch: | 10312 |
|---|---|
| Storage conditions: | (40 ± 2)° C./(75 ± 5) % RH |
| Package: | jelly capsules |

| Test items | Standard | 0 months | 3 months | 6 months |
|---|---|---|---|---|
| 1. Disintegration, min, not more than | 15 | 1 | 3 | 1 |
| 2. Dissolution of galantamine hydrobromide, %, of the stated content in 30 min, not less than | 75 (Q) | 98.8 | 105.1 | 102.8 |
| 3. Related substances, %, not more than: | | | | |
| impurity E (N-desmethylgalantamine) | 0.6 | 0.21 | 0.20 | 0.27 |
| unspecified impurity | 0.2 | 0.05 | 0.05 | 0.05 |
| total impurities | 1.5 | 0.27 | 0.25 | 0.32 |
| Assay of galantamine in one film-coated tablet, mg | From 9.5 to 10.5 | 9.972 | 9.890 | 9.835 |

TABLE 5

Composition with galantamine hydrobromide 20 mg capsules, according to Example 42

| Monitor batch: | 10315 |
|---|---|
| Storage conditions: | (25 ± 2)° C./(60 ± 5) % RH |
| Package: | Blister-green, semi-transparent PVC and aluminum film |

| Test items | Standard | 0 months | 6 months | 9 months | 12 months |
|---|---|---|---|---|---|
| 1. Disintegration, min, not more than | 15 | 1 | 1 | 1 | 1 |
| 2. Dissolution of galantamine hydrobromide, %, of the stated content in 30 min, not less than | 75 (Q) | 98.8 | 102.5 | 105.0 | 100.0 |
| 3. Related substances, %, not more than: | | | | | |
| impurity E (N-desmethylgalantamine) | 0.6 | 0.22 | 0.17 | 0.23 | 0.25 |
| unspecified impurity | 0.2 | 0.05 | 0.05 | 0.07; 0.05 | 0.07; 0.05 |
| total impurities | 1.5 | 0.27 | 0.22 | 0.35 | 0.37 |
| Assay of galantamine in one film-coated tablet, mg | From 19.0 to 21.0 | 19.982 | 19.860 | 19.865 | 19.955 |

We claim:

1. An oral pharmaceutical composition comprising, a therapeutically effective amount of a natural plant alkaloid or acceptable salt thereof, pharmaceutically acceptable excipients, and optionally at least one biologically active amino acid,
    wherein:
        the natural plant alkaloid or acceptable salt thereof comprises 1.5 mg to 3.0 mg cytisine or an acceptable salt thereof,
        the pharmaceutically acceptable excipients comprise cellulose powder in an amount of 5.0% to 92.5% by weight of the oral pharmaceutical composition, calcium sulphate in an amount of 5.0% to 92.5% by weight of the oral pharmaceutical composition, silica colloidal in an amount of 0.5% to 3.0% by weight of the oral pharmaceutical composition, and magnesium stearate in an amount 0.5% to 3.0% by weight of the oral pharmaceutical composition, with the cellulose powder and the calcium sulphate representing 64.5% to 97.5% by weight of the oral pharmaceutical composition, the cytisine or acceptable salt thereof is composed of particles, at least 90% of which are of not more than 100 µm in diameter, the oral pharmaceutical composition has a level of cytisine dissolution such that not less than 75% of the cytisine or acceptable salt thereof has dissolved after 45 minutes, the oral pharmaceutical composition has a uniform distribution of the natural plant alkaloid or acceptable salt thereof with no deviations out of ±5.0% of an average alkaloid content, and the oral pharmaceutical composition is lactose-free.

2. The oral pharmaceutical composition of claim 1, wherein the oral pharmaceutical composition is in the form of tablets or hard capsules.

3. The oral pharmaceutical composition of claim 1, wherein the at least one biologically active amino acid comprises 0.2 mg to 0.4 mg L-carnitine, 5 mg to 55 mg tryptophan, or a combination thereof.

* * * * *